(12) United States Patent
Wyatt et al.

(10) Patent No.: US 7,914,475 B2
(45) Date of Patent: Mar. 29, 2011

(54) ORTHOPEDIC BRACE

(75) Inventors: Stacy Wyatt, Camarillo, CA (US); Tracy Grim, Thousand Oaks, CA (US); Wendee Lee, Upland, CA (US)

(73) Assignee: Ossur hf, Reykjavik (IS)

( * ) Notice: Subject to any disclaimer, the term of this patent is extended or adjusted under 35 U.S.C. 154(b) by 1042 days.

(21) Appl. No.: 11/723,596

(22) Filed: Mar. 21, 2007

(65) Prior Publication Data
US 2007/0239093 A1 Oct. 11, 2007

Related U.S. Application Data

(60) Provisional application No. 60/784,447, filed on Mar. 22, 2006.

(51) Int. Cl.
*A61F 5/37* (2006.01)
*A61F 13/00* (2006.01)
*A61F 5/00* (2006.01)
*A61F 13/06* (2006.01)
*A61B 19/00* (2006.01)

(52) U.S. Cl. .......... 602/21; 128/846; 128/869; 128/878; 128/879; 602/5; 602/12; 602/20; 602/60; 602/61; 602/62; 602/64

(58) Field of Classification Search .................. 602/1, 5, 602/12, 20–22, 60–64; 128/846, 869, 878, 128/879
See application file for complete search history.

(56) References Cited

U.S. PATENT DOCUMENTS

| 4,013,070 | A | | 3/1977 | Harroff |
|---|---|---|---|---|
| 4,953,568 | A | | 9/1990 | Theisler |
| 4,960,114 | A | | 10/1990 | Dale |
| 5,036,838 | A | | 8/1991 | Sherman |
| D339,866 | S | | 9/1993 | Rice |
| 5,307,521 | A | | 5/1994 | Davis |
| D357,745 | S | | 4/1995 | Radwell |
| 5,513,657 | A | * | 5/1996 | Nelson ........................... 128/879 |
| 5,662,599 | A | | 9/1997 | Reich et al. |
| 5,728,059 | A | | 3/1998 | Wiesemann et al. |
| 5,733,249 | A | | 3/1998 | Katzin et al. |
| 5,759,166 | A | * | 6/1998 | Nelson et al. ................... 602/21 |
| 5,813,050 | A | | 9/1998 | Popowski |
| D405,180 | S | * | 2/1999 | Reina ............................ D24/190 |

(Continued)

OTHER PUBLICATIONS

"Basic Hand Anatomy," American Society for Surgery of the Hand, date unknown.

(Continued)

*Primary Examiner* — Patricia M Bianco
*Assistant Examiner* — Brandon Jackson
(74) *Attorney, Agent, or Firm* — Bacon & Thomas, PLLC

(57) ABSTRACT

An orthopedic brace is adaptable for either left or right sided use. The brace includes a softgood pad having a distal edge, a proximal edge opposite the distal edge, a dorsal edge, and a radial edge opposite the dorsal edge. A strap retainer is disposed on the radial or ulnar edge, and a strap pod is removably attachable to the pad in a left or right sided closure position. The strap pod cooperates with the strap retainer to secure the pad closed about a left limb, when the strap pod is attached in the left sided closure position, or about a right limb, when the strap pod is attached in the right sided closure position. A distal retention strap extends from the pad proximate to the distal and radial edges, and a reversible fastening member is coupled to the distal retention strap.

18 Claims, 7 Drawing Sheets

U.S. PATENT DOCUMENTS

| | | | |
|---|---|---|---|
| 5,873,130 A | 2/1999 | Lafferty | |
| 5,928,172 A | 7/1999 | Gaylord | |
| 6,024,715 A * | 2/2000 | Maxwell | 602/64 |
| 6,059,694 A | 5/2000 | Villepigue | |
| 6,186,969 B1 | 2/2001 | Bell et al. | |
| 6,261,252 B1 * | 7/2001 | Darcey | 602/6 |
| D456,081 S | 4/2002 | Bell et al. | |
| 6,561,994 B1 | 5/2003 | Mills et al. | |
| D477,088 S | 7/2003 | Brown et al. | |
| D477,409 S | 7/2003 | Mills et al. | |
| 6,730,053 B1 * | 5/2004 | Bodenschatz et al. | 602/64 |
| D496,465 S | 9/2004 | Weaver, II | |
| 6,893,410 B1 | 5/2005 | Hely | |
| 6,960,176 B1 | 11/2005 | Hely et al. | |
| D533,280 S * | 12/2006 | Wyatt et al. | D24/190 |
| 7,318,812 B2 | 1/2008 | Taylor et al. | |
| 7,473,236 B1 * | 1/2009 | Mathewson | 602/62 |
| 2004/0049141 A1 | 3/2004 | Slautterback et al. | |
| 2005/0197608 A1 | 9/2005 | Taylor et al. | |
| 2005/0197609 A1 | 9/2005 | Mills | |
| 2005/0273030 A1 | 12/2005 | Koby et al. | |

OTHER PUBLICATIONS

European Search Report issued related European application No. 07753684.5, Aug. 5, 2010, 6 pages.

* cited by examiner

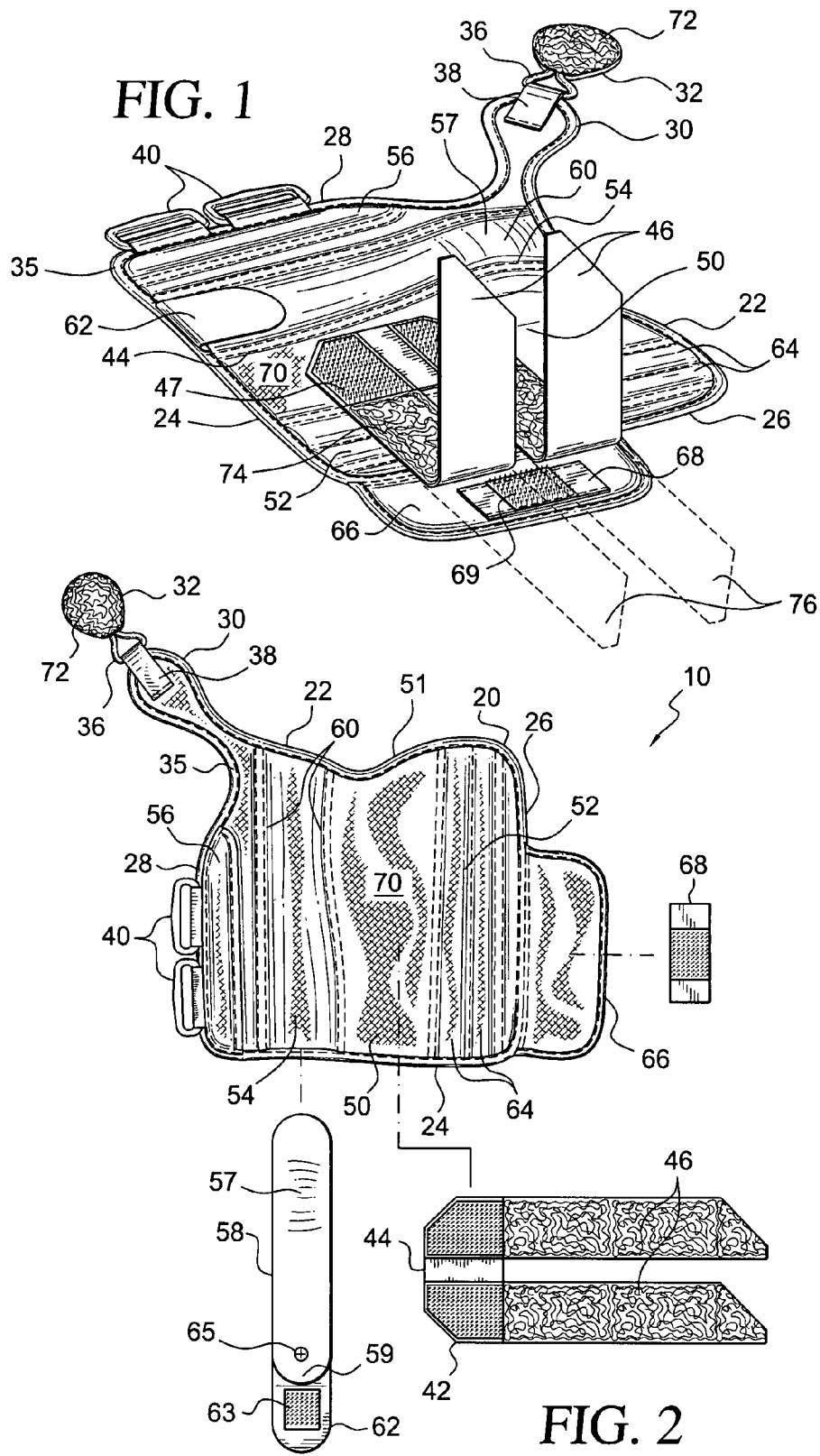

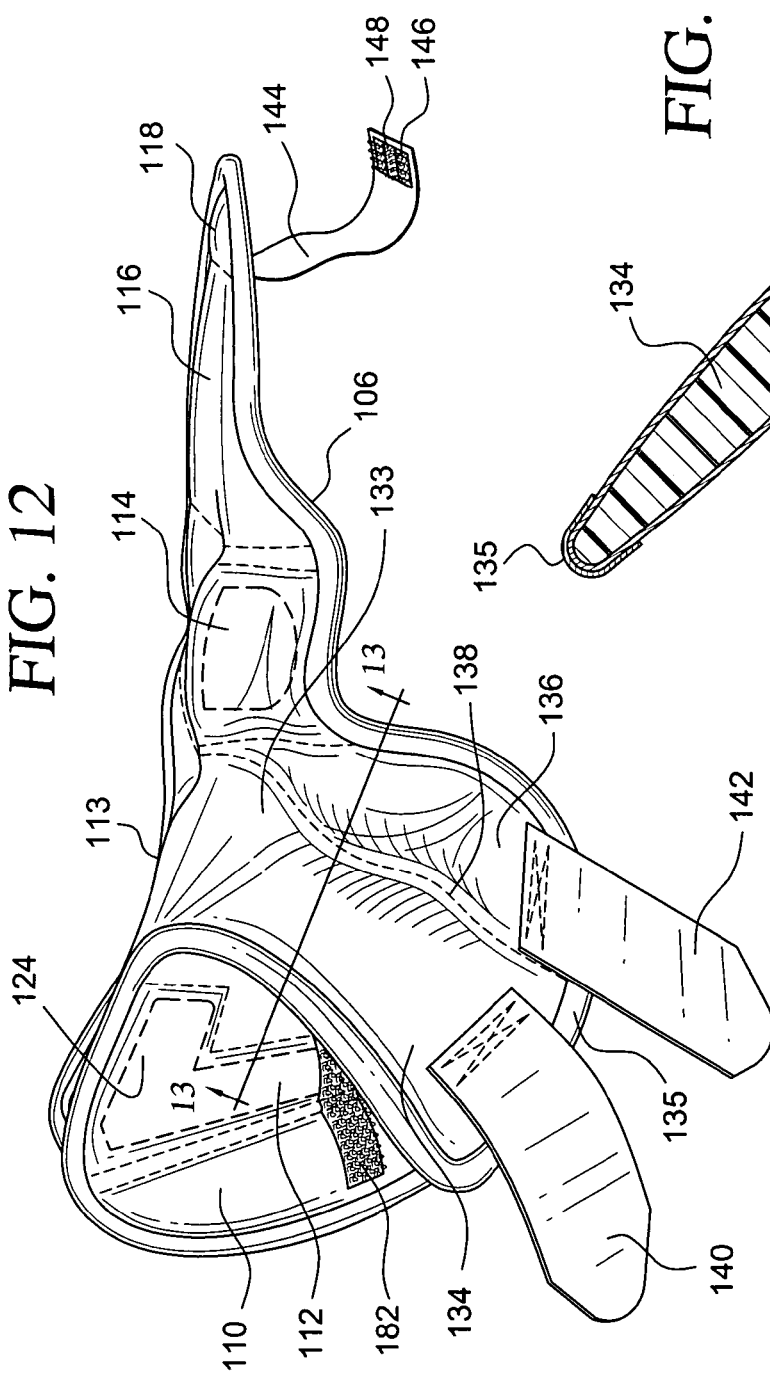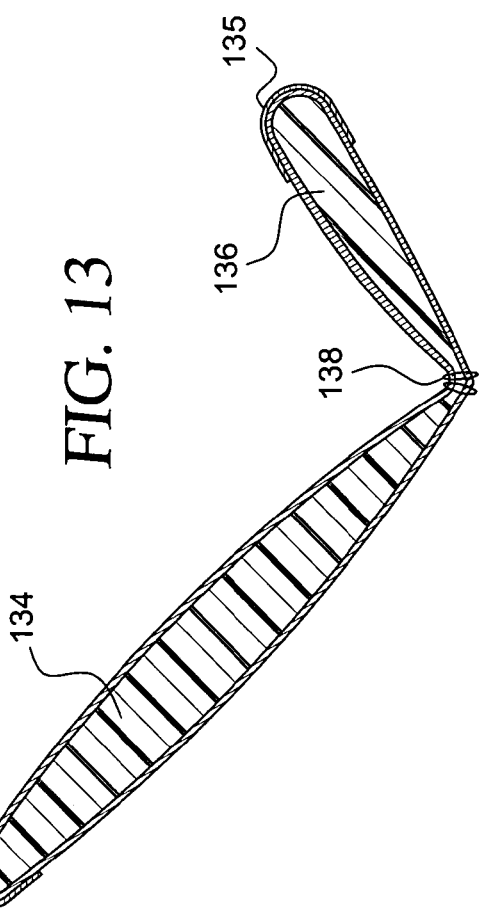

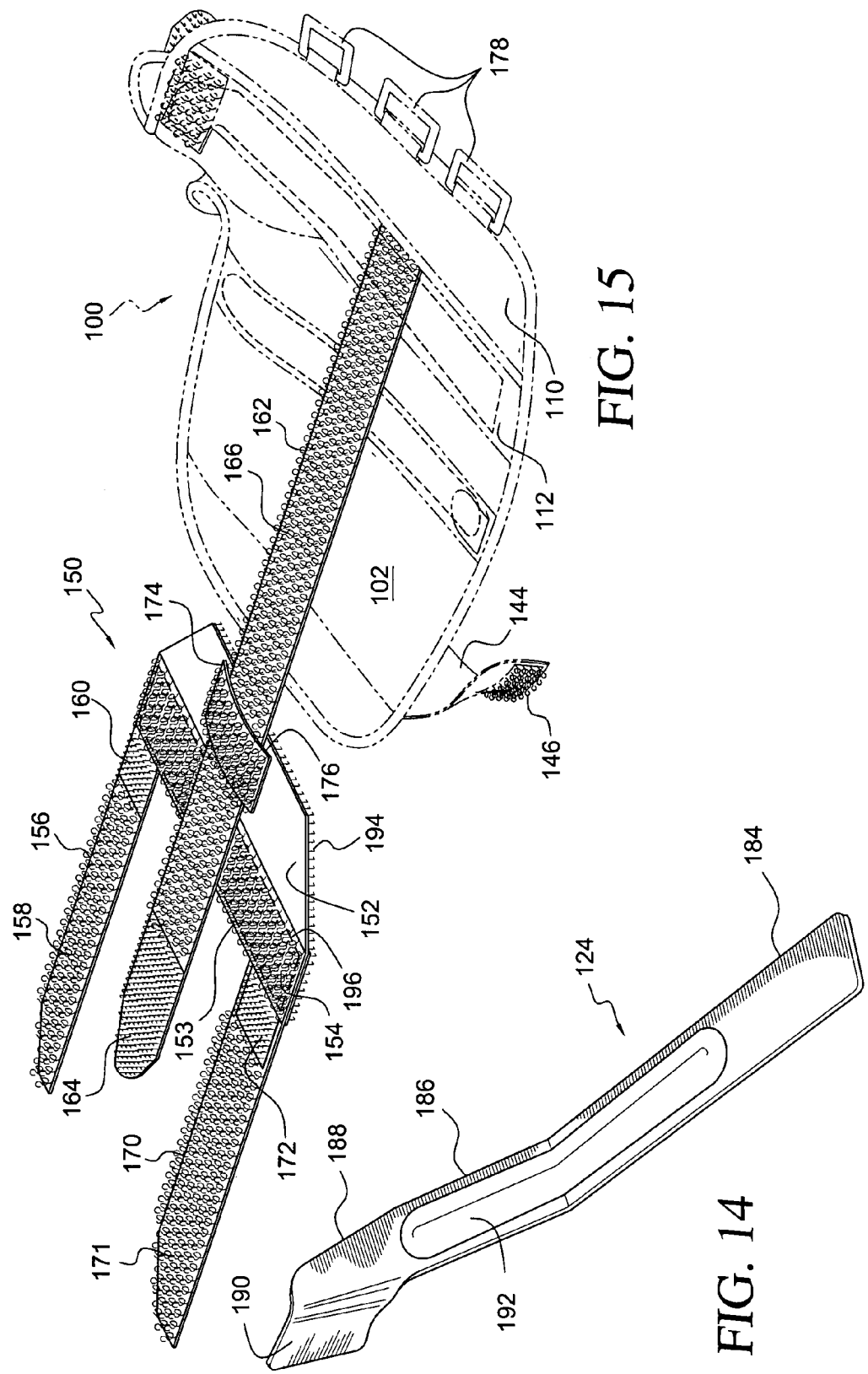

ORTHOPEDIC BRACE

CROSS REFERENCE TO RELATED APPLICATIONS

This application claims the benefit of priority of U.S. provisional application 60/784,447, filed on Mar. 22, 2006.

FIELD OF THE INVENTION

The present invention relates to orthopedic braces. More specifically, the invention relates to an orthopedic brace that is adaptable for either left or right sided use, and is readily adjustable to accommodate a variety of straps that may secure to a plurality of locations and sides of a softgood pad in order to provide adjustability for various hand and wrist sizes.

BACKGROUND

Numerous orthopedic supports and braces have been devised to provide therapeutic support or immobilization of a limb or extremity of a patient. Such supports and braces range from simple elastic or softgood bandages and braces to complicated mechanical devices. Hand and wrist braces including means for supporting a thumb or other digit, for example, often comprise an elastic or softgood member that may wrapped about the patient's hand, wrist, or other digit. These braces may be supplemented for one or more particular therapeutic purposes by the addition of rigid or semi-rigid support members, stays, splints, or the like.

It is generally desired for an orthopedic brace to be applied to a limb or extremity in a particular position or orientation to achieve a good fit. For example, a wrist brace that includes a palmar stay intended to support the hand in a "cock-up" position, must be positioned so that the palmar stay is located along the palmar side of the wrist and hand, and so that a bend in the distal portion of the palmar stay is angled toward, rather than away from, the palm of the hand. Similarly, a wrist brace that includes dorsal supports must be worn such that the dorsal supports are located along the dorsal side of the wrist.

Even a brace that includes no support members, such as the aforementioned palmar and dorsal stays, may be shaped according to particular features of a limb. For example, a wrist brace often extends well onto the hand, and may have a distal portion that is contoured or configured to be wrapped about the hand between the thumb and forefinger.

Given the need to apply an orthopedic brace in a particular position or orientation relative to a part of a limb, known orthopedic braces are typically configured for only left or right sided use. Unfortunately, may known left and right sided braces are not interchangeable; that is, a left handed wrist brace cannot be used on a right wrist.

This can be more fully appreciated by recalling the example previously described wherein a wrist brace includes a palmar stay intended to support the hand in a "cock-up" position. In this example, to simply apply a left handed brace to the right wrist "backwards," by turning the left handed brace "inside out," for example, does not reverse the palmar stay and would be ineffective because the palmar stay is not reoriented into the correct position for the right hand.

Further, and more generally, straps or fasteners that are located on the outside of a left handed brace, when applied to the left hand, would be located on the inside of the left handed brace when "turned inside out" for right handed use, therefore becoming useless or causing discomfort for a wearer of the brace. Thus, it is necessary for physicians, physical therapists, medical suppliers, and the like, to maintain a supply of both left and right handed braces.

Many known braces restrict the locations at which straps are secured to a main body softgood pad. These braces generally employ patches of corresponding hook and loop material on the straps and the main body, respectively. By restricting the locations of hook and loop material, a wearer is limited at where the strap will secure on the main body. Moreover, the general brace also lacks the flexibility to accommodate different straps and extensions from the main body that allow for securing a variety of different appendages.

In addition to the drawback of known braces typically being restricted for either left or right handed use, many known braces are limited as to their ability to accommodate certain sizes of appendages. As is well understood, injured wrists, hands or digits (i.e., thumb and fingers), often swell as they heal. It follows that a brace used to support these appendages must be adaptable to various sizes of injured wrists, hands or digits as they undergo healing. Moreover, dressings in addition to the brace and proximate to the skin of the wearer may be used in combination with the brace, wherein the brace extends over such dressings. In view of these size variations of both the wrists, hands or digits, and the possibility of dressings being used in combination with the brace, it is desirable to provide a brace that enables a wide range of size adjustability.

SUMMARY

In accordance with the invention, embodiments of orthopedic braces are described herein which have numerous configurations that may permit the usage of the brace for both left and right handed use. These embodiments include a variety of strap arrangements that may be used with a softgood pad that has surfaces generally defined by continuous loop or hook receivable material. These strap arrangements provide for adjustability as to sizing thereby allowing a single brace to accommodate a wider variety of sizes than by known braces.

Pursuant to one embodiment, an orthopedic brace is provided that may be selectively configured for use in either a left or right sided limb or extremity, such as a left or right wrist, and to accommodate a variety of wrist sizes. This wrist brace comprises a main body softgood pad. At least one strap retainer is disposed on a radial or an ulnar side of the pad, and a strap pod is removably attachable to the pad in either of a left sided closure position and a right sided closure position. The strap pod includes at least one strap depending therefrom that cooperates with the strap retainer to secure the pad in a closed position.

The wrist brace includes an intermediate strap that is secured to the pad near the radial edge thereof. A corresponding strap retainer is provided for receiving the intermediate strap. The strap pod defines a slot adapted for receiving the intermediate strap, wherein the strap pod is slidable relative to the intermediate strap and the pad. The wrist brace may also include a dorsal flap that connects to the radial and ulnar sides of the pad. The dorsal strap has a hook fastener which connects to at least one of the radial and ulnar sides of the pad.

According to another feature of the wrist brace, a distal retaining strap extends from the pad and has a reversible fastening member configured to secure the distal retaining strap to either surface of the pad. This distal retaining strap facilitates closure of the pad and secures the distal retaining strap in either the left or right sided closure position, and allows for a variety of brace sizes.

In another embodiment of the orthopedic brace, the brace is adapted for securing a thumb. This thumb brace includes a thumb stay disposed in a thumb stay pocket formed by the pad. A distal closure member may extend from or near the distal edge of the pad, and include a radial extension depending from the pad. An intermediate flap extends from the radial extension and is configured to extend about the thumb stay. The intermediate flap may have at least one strap securable to substantially the entirety of the first and second sides of the pad.

According to one feature of the thumb brace, the intermediate flap may include a crease that divides the intermediate flap into first and second sections. The first and second sections each include at least one strap extending therefrom, and may be configured to generally extend about the thumb stay to secure to any location on the pad.

In any of the embodiments of the orthopedic brace, the pad may include mutually opposed surfaces that are entirely or substantially formed of, or covered with, a loop fastening material thereby enabling a hook fastening material to be adhered to any part of either of the surfaces of the pad. Thus, components of the orthopedic brace, such as the strap pod and the straps depending therefrom, may employ a hook fastening material so that the components are selectively fastened to either side of the pad to thereby facilitate reconfiguration of the brace for left and right sided use.

As a result of the surface configuration of the pad, the orthopedic brace may be adaptable for either left or right sided use by positioning the strap pod on the pad in either the left or right sided closure position, or rotating the reversible fastening member to secure the distal retaining strap in either position.

Hence, certain embodiments described herein and the features thereof result in a single brace that may be used for both left and right sided applications, otherwise known as "universal," eliminating the need for physicians, physical therapists, medical suppliers, and others, to maintain a supply of both left and right sided braces. The embodiments herein also enable a single brace to accommodate a wide variety of hands, wrist and digits thereby reducing the amount of sizes that are necessary for storage, and enabling the wearer to adjust the brace according to degrees of swelling or simply to allow for greater comfort. Yet another advantage to the universal fitting and wide range of fitting of the brace is that a plurality of the universal orthopedic braces suitable for both left and right sided application may be more compactly packaged and stored.

These and other features, aspects, and advantages of the present invention will become better understood with regard to the following description, appended claims, and accompanying drawings.

BRIEF DESCRIPTION OF THE DRAWINGS

FIG. 1 is a perspective view of an embodiment of an orthopedic brace.

FIG. 2 is an assembly plan view of the brace of FIG. 1.

FIG. 12 is a top plan of the brace of FIG. 10.

FIG. 13 is a sectional view taken along line 13-13 in FIG. 12.

FIG. 14 is a thumb stay for the brace of FIG. 10.

FIG. 15 is a perspective view of the strap pod for the brace of FIG. 10.

DETAILED DESCRIPTION OF VARIOUS EMBODIMENTS

Figure 3:
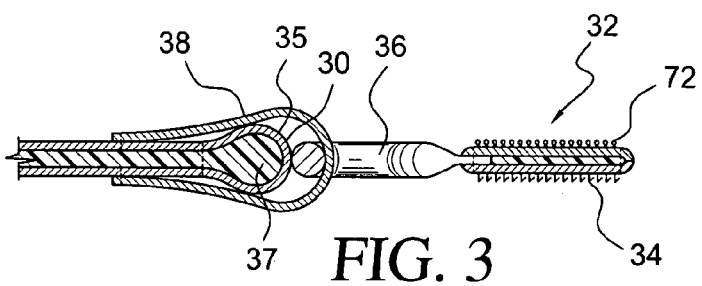
FIG. 3 is a sectional view of the reversible fastening member in the brace of FIG. 1.

A better understanding of different embodiments and methods of the invention may be had from the following description read in conjunction with the accompanying drawings in which like reference characters refer to like elements.

While the disclosure is susceptible to various modifications and alternative constructions, certain illustrative embodiments thereof are shown in the drawings and will be described below in detail. It should be understood, however, that there is no intention to limit the disclosure to the specific embodiments and methods disclosed, but on the contrary, the intention is to cover all modifications, alternative constructions, combinations, and equivalents falling within the spirit and scope of the disclosure and defined by the appended claims.

It will be understood that, unless a term is expressly defined in this disclosure to possess a described meaning, there is no intent to limit the meaning of such term, either expressly or indirectly, beyond its plain or ordinary meaning.

Referring to FIGS. 1 and 2, one embodiment of the orthopedic brace is embodied as a wrist brace 10. The wrist brace 10 may be selectively configured for use about either a left or right limb or extremity, and to accommodate a variety of wrist sizes.

The illustrated embodiment is a wrist brace that is adapted to be wrapped about a person's wrist to stabilize or support the wrist and hand, and can be configured for either the left wrist or the right wrist by simply reconfiguring or repositioning certain components of the brace. It will be understood that the inventive features herein may be employed in other orthopedic braces which are capable of configuration for both left and right limbs, such as for ankles and feet.

The illustrated embodiment of the wrist brace 10 comprises a generally rectangular softgood pad 20 having a distal edge 22, a proximal edge 24 opposite the distal edge 22, a dorsal edge 26, and a radial edge 28 opposite the dorsal edge 26. Surfaces of the pad 20 of this embodiment comprise a material (such as unbroken loop fabric, pile fabric, or any other material which is hook receivable, hereafter loop fastening material) to which a hook fastening material (the hook portion of a hook and loop type fastening material commonly referred to by the trademark VELCRO) may be removably adhered. The surfaces of the pad 20 are generally denoted in the drawings as an unbroken loop material under reference numeral 70.

While in specific embodiments the loop fastening material may be confined to certain areas or patches located on specific parts of the surfaces of the pad 20 to define certain fastening areas, the surfaces may be entirely formed of, or covered with, the loop fastening material such that a hook fastening material may be adhered to any part of the surfaces of the pad 20. Preferably, such loop fastening material is an unbroken loop material that prevents catching of the brace on sharp objects (as may occur with broken loop material), and further provides a texture that is pleasing to the wearer of the brace.

A distal closure member or distal retaining strap 30 extends from a distal portion of the pad 20. In the illustrated embodiment of FIG. 1, the distal retaining strap 30 is a thumb strap extending from a position proximate to the distal and radial edges 22, 28.

The construction of the retaining strap provides a wrist brace that may be worn by wrapping the pad about the wrist and a lower portion of the hand, and securing the retaining strap from one side of the hand to the other between the thumb and forefinger. The retaining strap prevents the brace sliding off of the hand in the distal direction. It will be understood that the distal retaining strap may be differently configured for various other body portions different from a thumb, or the distal retaining strap may be eliminated entirely.

As depicted in FIG. 1, a reversible fastening member 32 is coupled to the distal retaining strap 30. The reversible fastening member 32 is configured to connect and secure the distal retaining strap 30 to either surface of the pad 20. The reversible fastening member 32 is preferably rounded and sufficiently large so as to facilitate its application and removal onto the pad 20.

In observing FIG. 3, hook fastening material 34 is disposed on one surface of the reversible fastening member 32 to removably adhere the reversible fastening member 32 to a surface of the pad 20. While the hook fastening material 34 could be applied to both surfaces of the reversible fastening member 32 (or to both surfaces of the distal retaining strap 30 itself), it is preferable that a surface of the reversible fastening member 32 has a smooth surface (such as in a loop material 72) instead of the hook fastening material 34. This construction minimizes areas of the hook fastening material 34 that are exposed while a person is wearing the universal wrist brace 10 so as to prevent the hook material from catching and damaging on clothing or other articles, and resulting in injury or trauma to the person of those in contact.

The reversible fastening member 32 is preferably coupled to the distal retaining strap 30 by a swivel cord 36 connected to the fastening member 32 via a swivel retainer 38. The swivel cord 36 enables the reversible fastening member 32 to be turned so that the hook fastening material 34 faces the pad 20 in either a left sided or a right sided configuration. The swivel cord 36 preferably comprises a cord loop that allows the reversible fastening member 32 to be turned relative to the swivel retainer 38. An alternative swivel cord may be employed such as a barrel swivel or other suitable swivel fastener.

Figure 8:
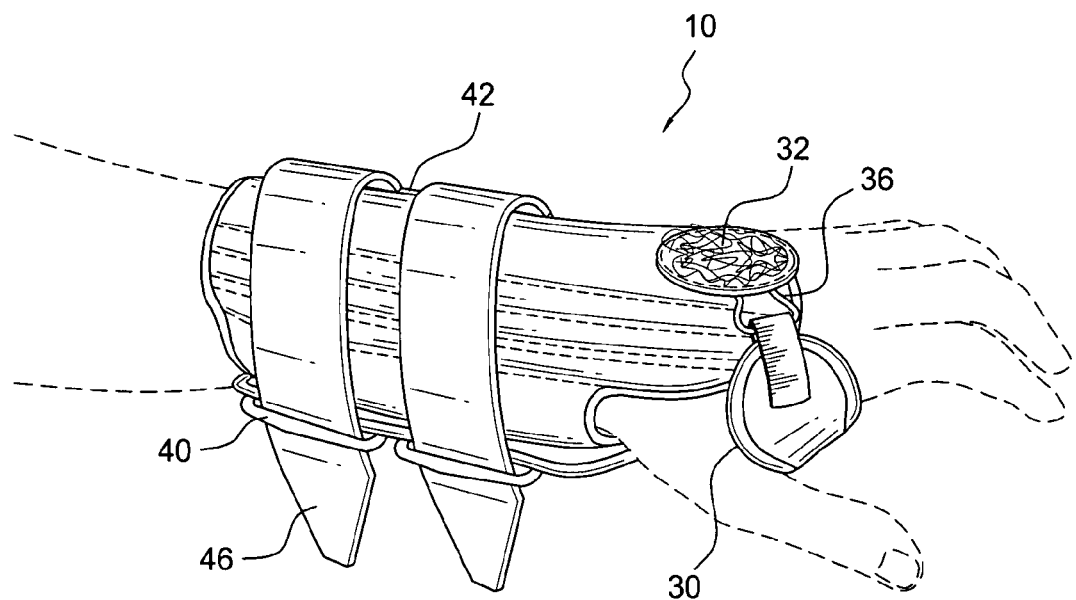
FIG. 8 is a perspective view of the brace of FIG. 1 positioned for use about a left wrist.
Figure 9:
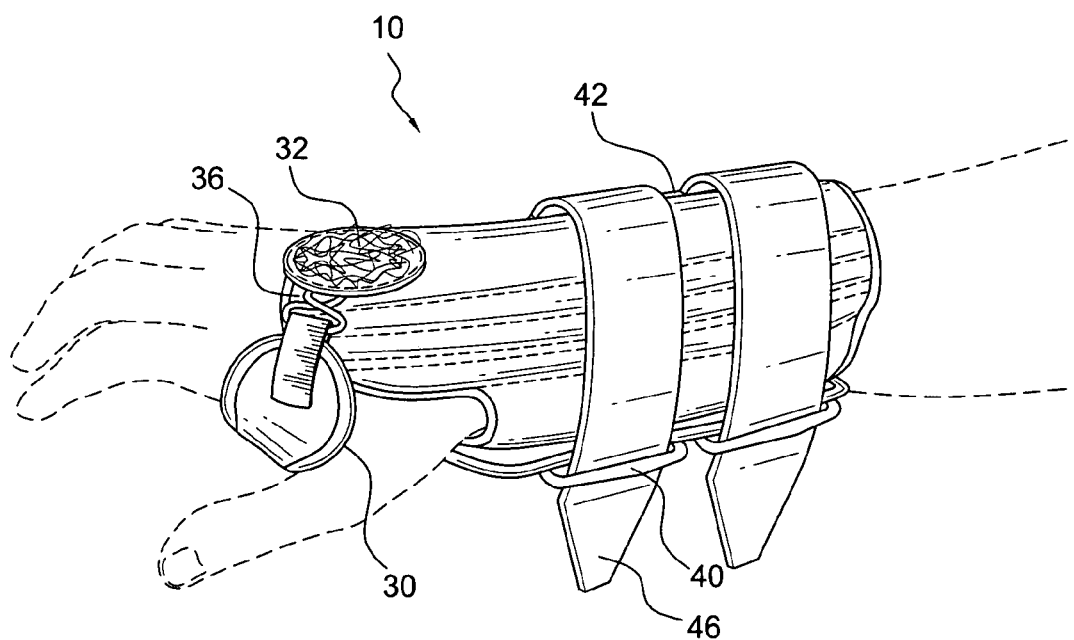
FIG. 9 is a perspective view of the brace of FIG. 1 positioned for use about a right wrist.

FIG. 8 exemplifies the reversible fastening member 32 in a normal configuration for placement on a left hand. Alternatively, FIG. 9 shows the reversible fastening member 32 "reversed," by twisting the cord loop for placement on a right hand.

In a variation of the hook fastening material 34, the reversible fastening member 32 may be provided on one or both sides with a snap fastener or the like, and corresponding fasteners may be provided on the pad 20. In another variation, the distal retaining strap 30 may be separate from the pad 20, and removably attached to the pad 20 in either of a left or right sided orientation by a hook fastening material disposed on the distal retaining strap 20. In yet another variation, the swivel retainer 38 may include releasable means for detaching the swivel cord 36, such that the releasable means includes a snap fastener or a hook-and-loop connection.

As noted previously, the pad 20 is adapted to be secured about either of a left wrist or a right wrist, or other extremity or limb by a closure system that can be configured for either left or right sided use. In the exemplary embodiment of the wrist of FIGS. 1 and 2, the closure system comprises at least one strap retainer 40 disposed on either the radial edge 28 or the dorsal edge 26 of the pad 20. The strap retainer 40 is embodied as a pair of loops disposed on the radial edge 28 for receiving a belt or strap member.

In observing FIGS. 4-7 in combination with FIGS. 1 and 2, a strap pod 42 is provided to cooperate with the strap retainer 40 to secure the pad 20 in a closed position. The strap pod 42 is removably attachable to the pad 20 in either of a left or a right sided closure position. This arrangement allows the wrist brace 10 to be configured for either left or right sided use by positioning the strap pod 42 on the pad 20 in either the left or the right sided closure position (i.e., on suitable sides of the pad 20).

Figure 4:
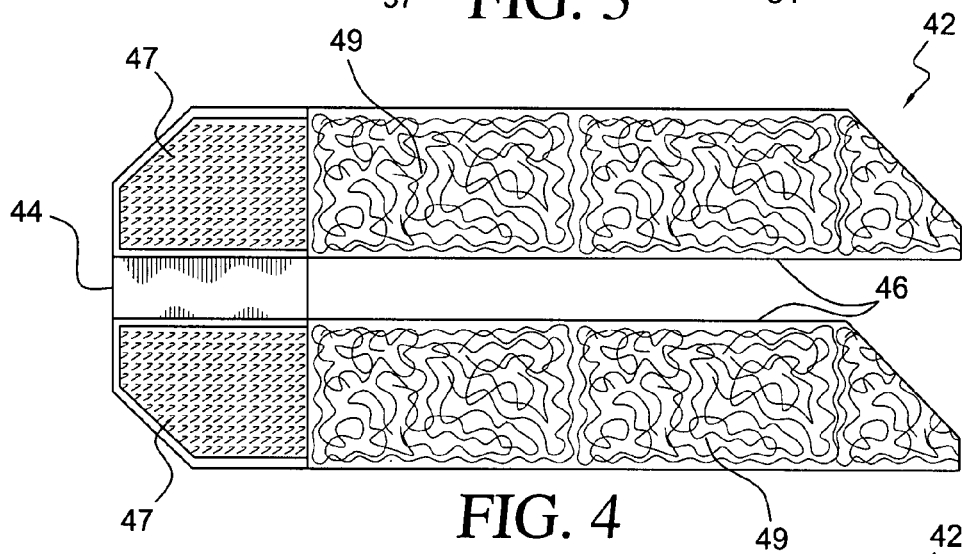
FIG. 4 is a plan view of a first side of the strap pod shown in FIG. 1.
Figure 5:
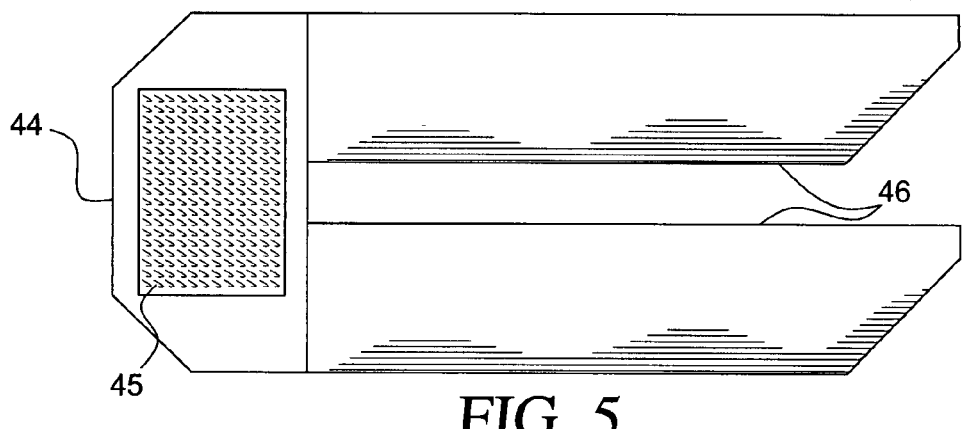
FIG. 5 is a plan view of a second side of the strap pod shown in FIG. 1.

The embodiment illustrated in FIGS. 4 and 5 shows a preferred strap pod 42 defined as a strap-type fastening member and having an attaching portion 44 for connecting the strap pod 42 to the pad 20. The strap pod 42 also includes at least one strap 46 extending from the attaching portion 44 and arranged to cooperate with the strap retainer 40 to secure the pad 20 in a closed position. While a pair of straps 46 are shown corresponding with the pair of loops shown in FIG. 2, other arrangements may be employed. Such other arrangements may include a single or a plurality of strap and strap retainer combinations.

The attaching portion 44 is removably attachable to a surface of the pad 20 in either of the left or the right sided closure positions. This is at least in part so the strap 46 can cooperate with the strap retainer 40 for securing the pad 20 in a closed position about a left wrist when the attaching portion 44 is connected in the left sided closure position, or about a right wrist when the attaching portion 44 is attached in the right sided closure position. The attaching portion 44 has a first side substantially covered with a hook fastening material 45 for removably connecting the attaching portion 44 to the pad 20.

At least one patch of the hook fastening material 47 is disposed on the other side of the attaching portion 44 corresponding with the strap 46. The strap 46 is made from, or has a surface at least partially covered with, a material that may be removably adhered to the hook fastening material 47. Further, the strap 46 may include loop material 49, either broken or unbroken, along the same side with the hook fastening material 47. The loop material 49 may be necessitated in the event that there are selectively located patches of corresponding hook material on the pad or on other attachments located on the pad.

In a variation of the strap 46, hook fastening material 47 may be located on a portion of at least one strap 46 in order to arrange the strap 46 in cooperation with other material or components of the strap 46. In another variation, the straps are fastened directly to the edge of the pad 20 opposite the strap retainer 40, and the fastening portion 44 is eliminated. It follows that by being fastened to an edge of the pad 20, there is no need to remove and relocate the straps 46. In yet another variation, the strap retainer 40 may be made to be removably attachable to the pad 20 and the strap pod fixed, or both may be removable.

Returning to FIGS. 1 and 2, a tongue 66 is provided which extends from an edge of the pad 20 opposite the strap retainer 40 so as to protect the radial side of the hand from closure members such as the strap retainer 40. According to this embodiment, the tongue 66 is a rectangular panel that extends from the dorsal edge 26 opposite the strap retainer 40. The tongue 66 is preferably made of a material that will distribute and spread the force of pressure points caused by the fastening members in order to increase patient comfort. A hook tab 68 is removably attachable to the tongue 66, and may be used to fasten the tongue 66 in place along the radial edge 28 when the wrist brace 10 is wrapped about a wrist.

Alternatively, the tongue 66 may be a substantially flexible material that essentially conforms to the anatomy of the wearer of the brace, and covers the corresponding anatomy of the wearer. The tongue may be permanently or removably secured to one or both of the radial and ulnar sides of the pad.

Figure 6:
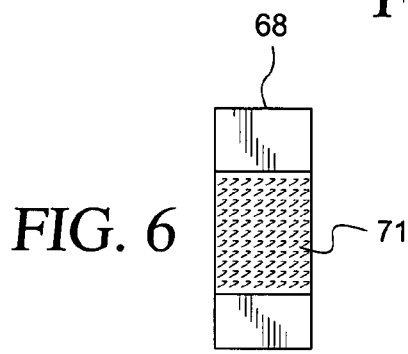
FIG. 6 is a plan view of a first side of the hook tab shown in FIG. 1.
Figure 7:
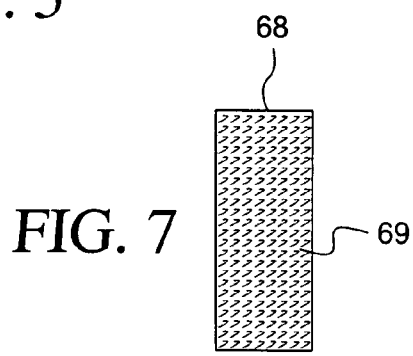
FIG. 7 is a plan view of a first side of the hook tab shown in FIG. 1.

In an embodiment illustrated in FIGS. 6 and 7, the hook tab 68 has a first side substantially covered with a hook fastening material 69 to secure the hook tab to the tongue 66, and a second side having a smaller area covered with the hook fastening material 71. The hook fastening material 69 is arranged for attachment to the tongue 66 on an outer side of the pad, the side depending on the left or right sided configuration of the wrist brace. Alternatively, the hook fastening material 71 is in contact with an inner side of the pad, again the side depending on the left or right sided configuration of the wrist brace.

The configuration of the hook tab 68 thereby allows it to be positioned on the tongue 66, and the tongue 66 to be secured to and removed from the radial edge 28 of the pad 20. This configuration minimizes a tendency for the hook tab 68 to be pulled from the tongue 66 during the process of applying and removing the wrist brace 10. As with other features described herein, the hook tab 68 remains removable for placement on either side of the tongue 66 to accommodate either left or right sided closure of the wrist brace 10.

The pad itself, in the embodiment shown in FIG. 1, may be configured for application as a wrist brace having a central ulnar section 50, a dorsal section 52 adjoining one edge of the ulnar section 50, a palmar section 54 adjoining an edge of the ulnar section 50 opposite the dorsal section 52, and a radial section 56 adjoining an edge of the palmar section 54 opposite the ulnar section 50. The distal retaining strap 30 extends from the pad to a position between the distal 22 and radial edges 28, adjacent to the palmar 54 and radial sections 56.

As best illustrated in FIG. 2, the pad 20 may define an ulnar dip 51 that is formed as a concave region along the distal edge 22 generally coincident with the ulnar section 50. The ulnar dip provides conformity with or accommodation of physical features of a wearer's hand.

A piping 35 is provided along the radial edge 28, the distal edge 22, the dorsal edge, proximal edge, and the edges defining outer portions of the tongue 66 and the distal closure member 30. The piping 35, as depicted in FIG. 3, may be arranged so as to bound the pad 20, and the sections associated therewith. The piping 35 may be an unbroken loop material or comprise other materials such as those that are not hook receivable.

The piping 35 may form a raised section 37 with the pad 20, and the stitching used to secure the piping onto the pad. The piping is arranged so as to place the edges of the pad comfortably against the wrist of the wearer. As an alternative, the pad may include areas that have a greater thickness than other areas, as exemplified by the raised portion. These raised areas may be provided at locations where additional padding and support is required.

Variations in the size of limbs may cause problems in fit of the wrist brace 10. For example, forearm size varies among people more significantly than wrist size. In certain embodiments, the pad may be provided with lengthwise slits (for example from the proximal toward the distal edge). While not specifically shown, a stretch material (as in the material represented by 144 in FIGS. 11 and 12) may be sewn into such slits to allow for expandability of the pad 20 to fit larger limbs. Alternatively, the seams dividing the sections of the pad may be replaced by stretchable material sewn to opposed edges of adjacent sections of the pad.

Splints, stays, or the like may be provided in any of the sections, either fixed within a section or removably inserted in a pocket formed within one of the aforementioned sections of the pad. In the illustrated wrist brace embodiment, a palmar stay 58 is removably disposed within a palmar pocket 60 coincident with the palmar section 54. The palmar pocket 60 has an opening along or near the proximal edge of the pad 20.

Because the palmar stay 58 is removable from the palmar pocket 60, it may be reversed so that any curvature of the palmar stay 58 may be properly oriented for therapeutic effect for either of a left or right sided application. An example of a palmar stay 58 curvature is exemplified by curvature 57 which generally corresponds to the palm of a hand. The configuration of the palmar stay 58 is particularly adapted to be reversible so that it will correspond to left and right handed configurations depending on its orientation.

As depicted in FIG. 2, a strap 62 is affixed to a proximal end 59 of the palmar stay 58 to facilitate withdrawal of the palmar stay 58 from the palmar pocket 60. The strap 62 may have a surface covered at least partially with a hook fastening material 63 that may be fastened to the pad 20, both to retain the palmar stay 58 in place within the palmar pocket 60 and to secure the strap 62. The strap 62 is exemplified as being pivotably secured to the palmar stay 58 via a fastener 65.

Dorsal stays 64 may be disposed within the dorsal section 52 to provide additional stiffening or support. The dorsal stays 64 are shown fixed within the dorsal section 52. Alternatively, the dorsal section 52 may be provided with a pocket for removal and replacement of the dorsal stays 64. Other splints, stays or supports may be provided elsewhere within the pad.

Dorsal stays 64 are preferably located near or adjacent to the ulnar side of the wrist brace. Depending on the size of the patient, a dorsal stay may become positioned directly over the ulnar side. Dual dorsal stays 64 allows conformance with the ulnar side and elimination of pressure on the ulnar side in both left and right sided configurations. In one dual stay configuration, the dorsal stays 64 are attached at the proximal end (in a "Y" or a "tuning fork" shape).

In the illustrated embodiment, a split dorsal stay comprises a pair of dorsal stays 64 that are located side-by side and parallel to one another. Other configurations may be employed, such as a single stay or additional plural stays. In a variation of the depicted wrist brace, pockets for the splints or stays are eliminated, and splints or stays attached directly to the surface of the pad with a hook fastening material.

Turning now to FIGS. 8 and 9, the wrist brace 10 is shown worn about a left wrist (FIG. 8) and a right wrist (FIG. 9). It can be recognized that configuration for left or right handed use requires: (1) positioning the strap pod 42 and the hook tab for left or right handed closure; (2) orienting the palmar stay within the palmar pocket 60 for left or right handed use; (3) positioning the pad about the wrist; and (4) positioning the reversible fastening member 32 so that its hook fastening material side faces the surface of the pad to secure the distal retaining strap 30 in place.

It can be seen that the position of the reversible fastening member 32, which secures the distal retaining strap 30 about the hand between thumb and forefinger, is reversed in the right handed application (FIG. 9) relative to the left handed application (FIG. 8) by twisting the cord loop swivel cord 36.

It can also be observed that the left handed closure position of the strap pod 42 is on the outside surface of the pad 20 when the pad 20 is wrapped about a left limb, while the right handed closure position of the strap pod 42 is simply the opposite surface, or the outside surface of the pad 20 when the pad 20 is wrapped about a right limb.

In addition to providing for left or right sided use, the removable strap pod 42 may be varied in position on either side of the pad to lengthen, or shorten, the extension of the straps 46 to obtain a proper fit. This adds to increased versatility by the preferred construction of the pad surfaces as generally being defined by the continuous unbroken loop material (inclusive of seams dividing portions of these surfaces).

Color coded markings or indicia may be provided on the pad, or on removable parts of the wrist brace, or on both, to indicate the correct attachment position for the various removable parts for both left and right sided configurations. Such color coded markings or indicia provide assistance to a patient in configuring the brace 20 for use.

Figure 10:
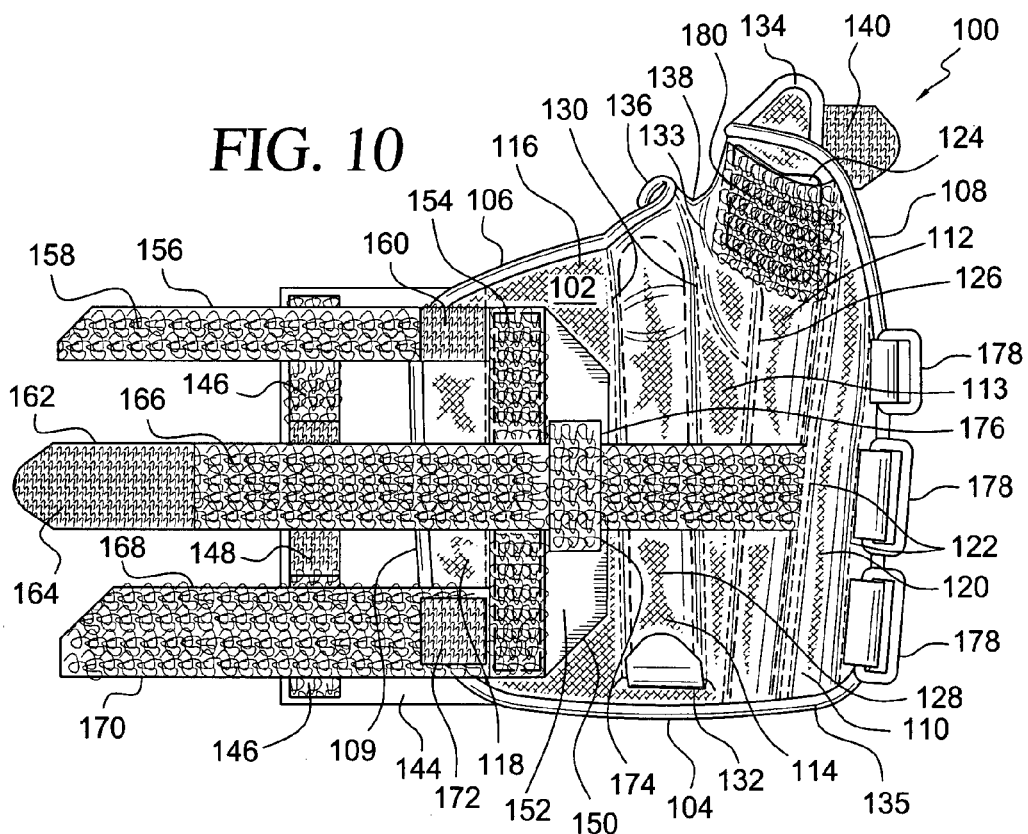
FIG. 10 is a side plan view of a first side of another embodiment of the orthopedic brace.
Figure 11:
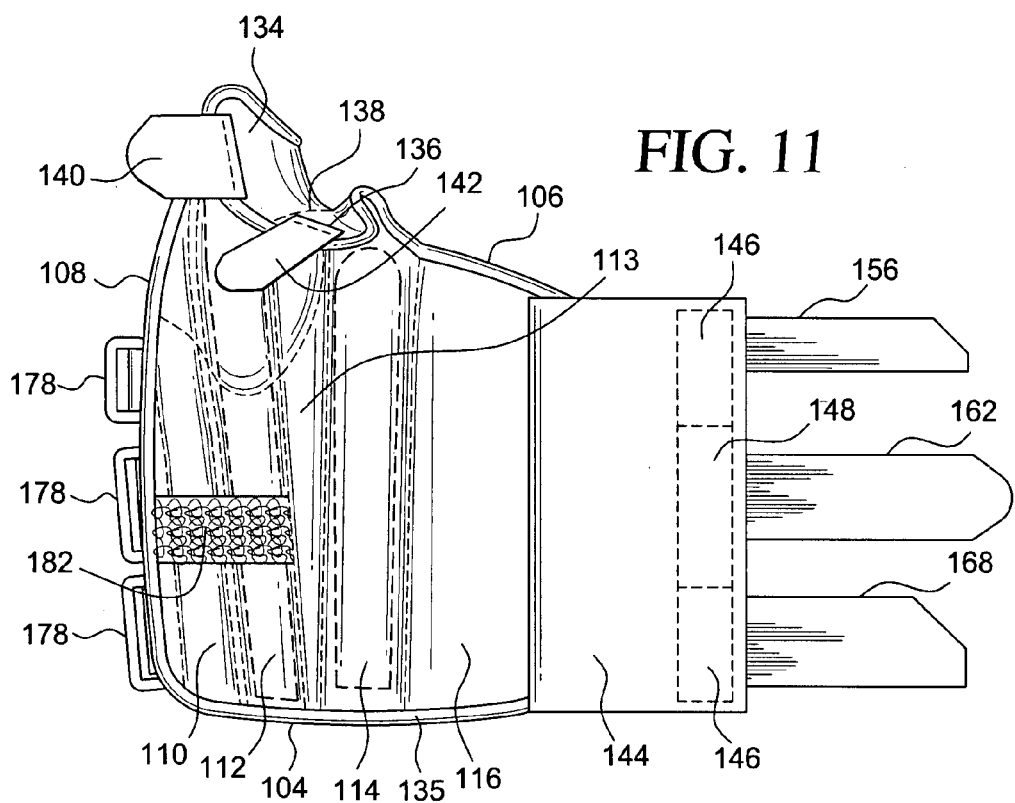
FIG. 11 is a side plan view of a second side of the brace of FIG. 10.

In accordance with another embodiment of the orthopedic brace according to the present invention, FIGS. 10 and 11 depict a thumb brace 100 that incorporates many of the features of the aforementioned wrist brace embodiments and the variations thereof. The thumb brace 100 includes a softgood pad 102 similarly constructed as the pad 20 of the wrist brace 10 so as to have generally continuous first and second surfaces constructed from an unbroken loop material.

The pad 102 includes a distal edge 106, a proximal edge 108, a radial edge 108, and a dorsal edge 109. While the pad 102 has generally continuous first and second surfaces, these surfaces are divided into sections including a first radial section 110, a second radial section 112, an intermediate section 113, a palmar section 114, an ulnar section 116, and a dorsal section 118. As with the sections of the wrist brace 10, the sections of the thumb brace are preferably divided by a plurality of seams.

As with the wrist brace 10, the thumb brace 100 includes a plurality of stays and pockets formed by the pad for receiving such stays. Preferably, the thumb brace 100 includes a first radial stay 120 and a corresponding first radial stay pocket 122, and a second radial stay 124 and a corresponding second radial stay pocket 126. The thumb brace 100 further includes a removable palmar stay 128, a corresponding palmar stay pocket 130, and a palmar pocket flap 132.

The palmar stay 128 may be configured as the palmar stay 58 in the wrist brace 10 including the flap connected to the palmar stay. Alternatively, the pocket flap 132 extends from the pad 102 and closes the palmar stay pocket 130.

In observing FIGS. 10-13, the thumb brace 100 includes a distal closure member in the form of an intermediate flap having first and second sections 134, 136 which extend from the distal edge 106 and near the radial edge 108. These first and second sections 134, 136 generally extend from the intermediate section 1.13, and are preferably divided by a defined crease 138 so as to remain generally continuous with one another. First and second section straps 140, 142, extend from the first and second sections 134, 136, respectively, and are adapted to secure to a plurality of locations along the pad 102.

As shown in FIGS. 12 and 13, the intermediate flap 134, 136 is a unitary flap that is divided along the crease 138 to substantially extend in two different directions. The first section 134 is configured along the crease 138 so as to wrap about a thumb. In particular, the first section 134 extends about the second radial stay 124 and the first strap 140 connects to either a loop island 180 generally extending across the first and second radial sections 110, 112. The loop island 180 is preferably a broken loop material so as to provide a strong connection with the hook material of the first strap 140.

The second section 136 essentially performs the function of the fastening member 32 in accordance with the wrist brace 10. As such, the second section 136 is adapted to the intermediate flap about the hand between thumb and forefinger to retain the brace on the hand and to further secure the thumb via its connection to the first section 134.

The continuous configuration of the intermediate flap by way of the crease 138 dividing the first and second sections 134, 136, provides improved comfort to the wearer over thumb strap systems wherein one or more thumb straps are employed. For example, FIG. 13 shows how the first and second sections 134, 136 may include padding that is less than, equal to, or in addition to padding that is used for the remainder of the pad 102. Further, the thickness of the first and second sections 134, 136 may be sized larger than the straps 140, 142, thereby more evenly distributing the pressure exerted to the hand. Moreover, the continuous configuration of the intermediate flap contributes to additional durability of the brace in that the straps need only be secured to the larger ends of the first and second sections, and are not required to extend between the thumb and the forefinger.

The thumb brace 100 preferably includes a dorsal flap 144 that depends from the dorsal section 118. The dorsal flap 144 is constructed from a stretchable material and is intended to cover a portion of the arm when the thumb brace 100 is worn. Alternatively, the dorsal flap 144 may be constructed in a similar manner to the tongue 66 in the wrist brace 10. The dorsal flap 144 includes a stiffener band 146 located at one edge thereof, with a hook flap 148 extending therefrom. The stiffener band 146 may comprise a loop material, a stay, or suitable material to reinforce the edge upon which it is secured. Due to the continuous unbroken loop material surfaces of the pad 102, the hook flap 148 may secure to a variety of locations along the pad 102.

Turning to FIG. 14, the second radial or thumb stay 124 is generally contoured to the radial aspect of the hand and includes first and second segments 184, 186. The tip of the second radial stay 124 is particularly contoured to accommodate the thumb aspect of the hand via a tapered segment or tip 188 and a thumb flange 190. The thumb flange 190 depends from the tapered segment 188 at generally 90° so as to accommodate a thumb. The second radial stay 124 may also include a concave portion 192 anatomically contoured to receive a portion of a thumb.

FIG. 15 illustrates a variation of a strap pod 150 that may be used in accordance with any of the embodiments described herein. Specifically, the strap pod 150 includes a main body 152 having a stiffened portion 153. The stiffened portion 153 preferably defines a first surface including a section defined by loop material (broken or unbroken) 154, and a second surface including a section of hook material 194. A stiffener element 196 is provided on or within the main body 152.

The strap pod 150 further comprises first and second straps 156, 170, extending from the main body 152. Each of the first and second straps includes a hook portion 160, 172, respectively, and a loop section 158, 171, respectively. The first and second straps 156, 170 are configured for being received by corresponding strap retainers 178 extending along the radial edge 108 of the pad 102.

An island 174 is secured to the main body 152, and forms a slot 176 relative to the main body 152. The slot 176 is configured for receiving a strap 162 secured near or on one of the first and second radial sections 110, 112 thereby enabling the strap pod 150 is slide along the strap 162. The strap 162 includes a hook material portion 164, and a loop material portion 166.

Since the strap pod 150 is slidable along the strap 162, and by virtue of the pad 102 surfaces being formed of continuous loop material, the strap pod 150 may be secured at a variety of locations along the pad 102. This provides considerable flexibility to where the strap pod may be secured, thereby allowing the wrist brace to be useable for a variety of wrist sizes.

Figure 16:
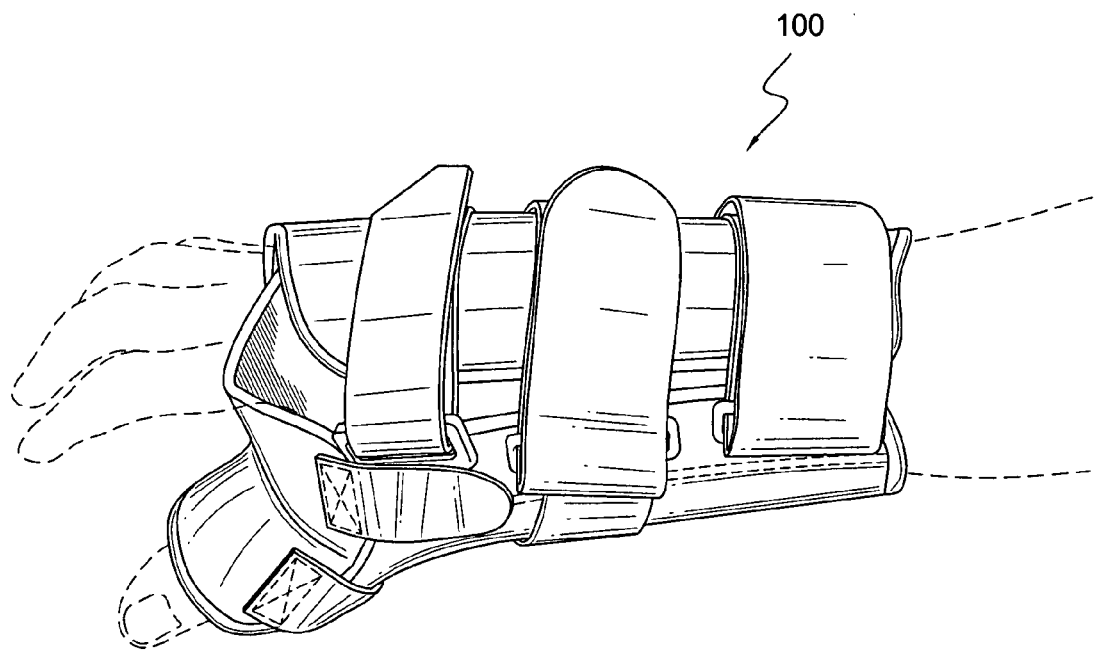
FIG. 16 is a first perspective view of the brace of FIG. 10 positioned for use on a right wrist.
Figure 17:
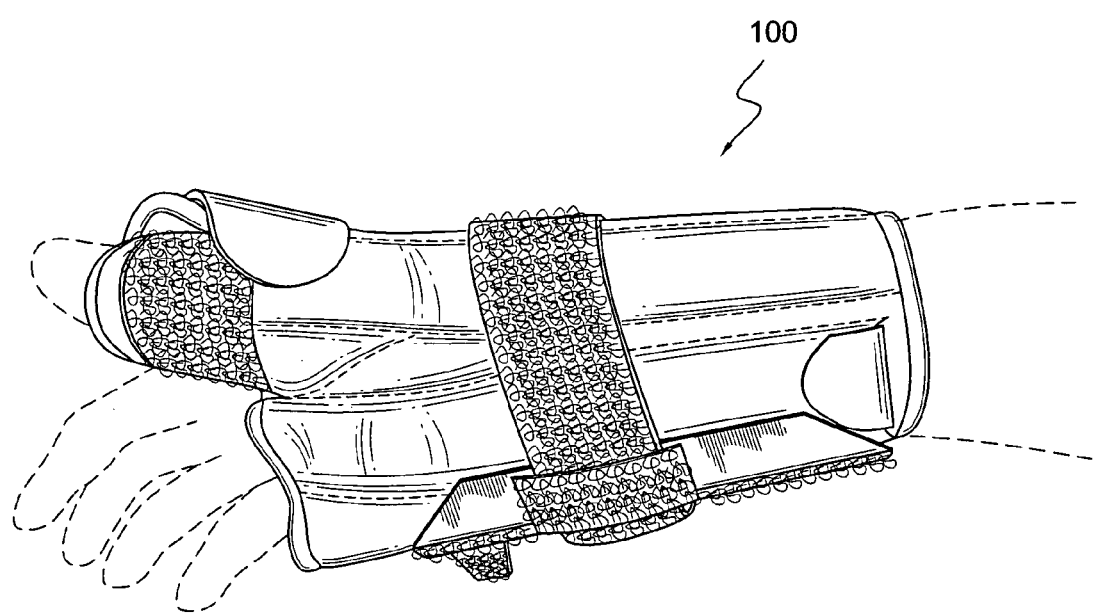
FIG. 17 is a second perspective view of the brace of FIG. 10 positioned for use on a right wrist.

FIGS. 16 and 17 exemplify the thumb brace 100 on a wrist and for securing a thumb. Moreover, the thumb brace 100 is shown as having all of the aforementioned straps secured to the continuous material forming the surfaces of the brace.

It is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various components from different embodiments described herein. In addition to the variations described herein, other known equivalents for each feature can be mixed and matched by one of ordinary skill in this art to construct an orthopedic brace in accordance with principles of the present invention. Therefore, the embodiments described herein may be adapted to orthopedic systems for securing, supporting or comforting limbs or other anatomy.

Although this invention has been disclosed in the context of certain preferred embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

We claim:

1. An orthopedic brace, comprising:
a pad having a distal edge, a proximal edge opposite the distal edge, a dorsal edge, and a radial edge opposite the dorsal edge, the pad further defining first and second surfaces;
at least one strap retainer disposed on the radial edge or the dorsal edge;
a strap pod having an attaching portion and at least one strap extending from the attaching portion, the attaching portion defining first and second surfaces such that the attaching portion first surface is immovably mountable on and removably attachable to one of the first and second surfaces of the pad in either of a left or a right sided closure position, the at least one strap cooperating with the at least one strap retainer for securing the pad in a closed position about a left limb when the attaching portion is attached in the left sided closure position or about a right limb when the attaching portion is attached in the right sided closure position, the at least one strap defining first and second surfaces such that the at least one strap second surface is immovably mountable on and removably securable to the attaching portion second surface;
a distal retaining strap extending from the pad from a position proximate to the distal and radial edges; and
a reversible fastening member coupled to the distal retaining strap by a swivel, the reversible fastening member defining a first surface having a hook fastening material disposed thereon, wherein the reversible fastening member is configured to secure the distal retaining strap to either the first or second surfaces of the pad;
wherein the orthopedic brace is adaptable for either left or right sided use by positioning the strap pod on the pad in either of the left or right sided closure positions.

2. The orthopedic brace according to claim 1, wherein the pad has a generally central ulnar section having a concave ulnar dip formed along the distal edge.

3. The orthopedic brace according to claim 2, wherein the pad has a palmar pocket formed along one side of the ulnar section and extending between the proximal and distal edges, the palmar pocket having an opening at the proximal edge for insertion of a palmar stay in either a left or a right sided orientation.

4. The orthopedic brace according to claim 2, wherein the pad has a dorsal section formed along one side of the ulnar section and extending between the proximal and distal edges, and at least one dorsal stay disposed within the dorsal section.

5. The brace according to claim 1, further comprising a palmar stay removably disposed in a palmar region of the pad, the palmar stay being reversible to accommodate left or right handed closure positions.

6. The orthopedic brace according to claim 1, further comprising a palmar stay pocket defined in a palmar region of the pad and adapted to removably receive a palmar stay, the palmar stay being reversible to accommodate left or right handed closure positions.

7. The orthopedic brace according to claim 1, further comprising at least one dorsal stay disposed in a dorsal region of the pad.

8. The orthopedic brace according to claim 1, further comprising a tongue extending from an edge of the pad, and a hook pad removably attached to a surface of the tongue.

9. The orthopedic brace according to claim 1, wherein the reversible fastening member includes color coded marking or indicia indicating the correct attachment position of the reversible fastening member for left and right handed closure positions.

10. The orthopedic brace according to claim 1, further comprising a non-hook receivable piping extending about at least some of the periphery of the pad.

11. The orthopedic brace according to claim 1, further comprising:
an intermediate strap secured to the pad near or at the radial edge thereof;
at least one strap retainer connected to the pad and arranged for receiving the intermediate strap;
wherein the strap pod defines a slot adapted for receiving the intermediate strap, the strap pod being slidable along the intermediate strap and relative to the pad.

12. An orthopedic brace, comprising:
a pad having a distal edge, a proximal edge opposite the distal edge, a dorsal edge, and a radial edge opposite the dorsal edge, the pad having first and second surfaces each comprising loop fastening material forming a generally continuous surface extending substantially the entirety of the corresponding surface;

a detachable strap pod having an attaching portion and at least one strap extending from the attaching portion, the attaching portion defining first and second surfaces such that the attaching portion first surface immovably mountable on and removably attachable to the loop fastening material of both the first and second surfaces of the pad, the at least one strap immovably mountable on and securable to the second surface of the attaching portion; a distal closure member extending from or near the distal edge of the pad, the distal closure member having at least one attachment member securable to the first and second surfaces of the pad;

an intermediate strap secured to the pad near or at the radial edge thereof;

at least one strap retainer connected to the pad and arranged for receiving the intermediate strap;

wherein the strap pod defines a slot adapted for receiving the intermediate strap, the strap pod being slidable along the intermediate strap and relative to the pad.

13. The orthopedic brace according to claim 12, wherein the distal closure member is a retention strap extending from the pad from a position proximate to the distal and radial edges, a reversible fastening member being coupled to the distal retention strap and configured to secure the distal retention strap to the first and second surfaces of the pad.

14. The orthopedic brace according to claim 13, wherein the reversible fastening member includes a first surface having a hook fastener disposed thereon.

15. The orthopedic brace according to claim 13, wherein the reversible fastening member is coupled to the distal retention strap by a swivel.

16. The orthopedic brace according to claim 12, wherein the second surface of the at least one strap is defined by an unbroken loop material, and the second surface of the attaching portion is defined by hook fastening material.

17. The orthopedic brace according to claim 12, further comprising a dorsal section removably connecting to the radial and ulnar sides of the pad.

18. An orthopedic brace, comprising:
a pad having proximal and distal edges, the pad having first and second surfaces each comprising loop fastening material forming a generally continuous surface extending across the entirety of the corresponding surface;
a strap pod having a generally planar and compliant attaching portion and at least one strap extending freely from the attaching portion, the attaching portion removably attachable to either surface of the pad for securing the pad in a closed position;
a swiveling fastening member freely connecting to the pad and configured to secure to the first and second surface of the pad at any location thereof
wherein the reversible fastening member includes a first surface having a hook fastener disposed thereon.

* * * * *